(12) United States Patent
Dhawan

(10) Patent No.: US 11,077,792 B2
(45) Date of Patent: Aug. 3, 2021

(54) DRIVER FOCUS ANALYZER

(71) Applicant: Arjun Kundan Dhawan, Newburgh, IN (US)

(72) Inventor: Arjun Kundan Dhawan, Newburgh, IN (US)

( * ) Notice: Subject to any disclaimer, the term of this patent is extended or adjusted under 35 U.S.C. 154(b) by 0 days.

(21) Appl. No.: 16/671,380

(22) Filed: Nov. 1, 2019

(65) Prior Publication Data

US 2020/0062178 A1 Feb. 27, 2020

Related U.S. Application Data

(63) Continuation of application No. 15/257,153, filed on Sep. 6, 2016, now abandoned.

(Continued)

(51) Int. Cl.
| | |
|---|---|
| *B60Q 9/00* | (2006.01) |
| *A61B 5/11* | (2006.01) |
| *A61B 5/18* | (2006.01) |
| *A61B 8/08* | (2006.01) |
| *A61B 5/00* | (2006.01) |
| *A61B 3/113* | (2006.01) |
| *A61B 5/16* | (2006.01) |
| *A61B 10/00* | (2006.01) |

(52) U.S. Cl.
CPC ............... *B60Q 9/00* (2013.01); *A61B 3/113* (2013.01); *A61B 5/1118* (2013.01); *A61B 5/163* (2017.08); *A61B 5/18* (2013.01); *A61B 5/4845* (2013.01); *A61B 5/6844* (2013.01); *A61B 5/6893* (2013.01); *A61B 5/6898* (2013.01); *A61B 5/746* (2013.01); *A61B 8/08* (2013.01); *A61B 5/0022* (2013.01); *A61B 5/742* (2013.01); *A61B 5/7405* (2013.01); *A61B 2010/0009* (2013.01); *A61B 2562/0204* (2013.01); *A61B 2562/0257* (2013.01)

(58) Field of Classification Search
None
See application file for complete search history.

(56) References Cited

U.S. PATENT DOCUMENTS

| | | | | |
|---|---|---|---|---|
| 5,482,314 A | * | 1/1996 | Corrado | G01S 15/523 280/735 |
| 5,531,225 A | * | 7/1996 | Nawata | G01N 33/4972 180/272 |

(Continued)

OTHER PUBLICATIONS

Dhawan; *A Warning System Based on Sensor Technology and Chemical Analysis to Detect Distracted Driving*; PowerPoint Presentation; Mar. 2015.

(Continued)

*Primary Examiner* — Muhammad Adnan
(74) *Attorney, Agent, or Firm* — Nelson Mullins Riley & Scarborough LLP

(57) ABSTRACT

A driver focus analyzer including one or more sensors configured to measure a distance of a driver or computing device from the one or more sensors, processing circuitry configured to compare the distance to a predetermined distance threshold, determine if the distance exceeds the predetermined distance threshold, and cause an alert in response to at least determining that the distance exceeds the predetermined threshold, and an alert output device configured to generate an audio or visual output in response to the alert.

3 Claims, 8 Drawing Sheets

Related U.S. Application Data

(60) Provisional application No. 62/281,835, filed on Jan. 22, 2016.

(56) References Cited

U.S. PATENT DOCUMENTS

| | | | | |
|---|---|---|---|---|
| 5,691,693 | A * | 11/1997 | Kithil | B60N 2/002 |
| | | | | 340/439 |
| 6,445,303 | B1 * | 9/2002 | Aryeh | G08B 21/06 |
| | | | | 180/272 |
| 6,794,728 | B1 * | 9/2004 | Kithil | B60H 1/00742 |
| | | | | 257/532 |
| 7,126,485 | B2 * | 10/2006 | Cece | G08B 21/06 |
| | | | | 340/576 |
| 7,596,242 | B2 * | 9/2009 | Breed | G06K 9/00362 |
| | | | | 382/103 |
| 7,970,175 | B2 * | 6/2011 | Malawey | G06K 9/00335 |
| | | | | 382/103 |
| 9,796,391 | B2 * | 10/2017 | Olson | B60K 35/00 |
| 10,040,350 | B2 * | 8/2018 | Dias | B60W 50/14 |
| 10,118,488 | B1 * | 11/2018 | Riley, Sr. | A61B 5/7455 |
| 10,836,403 | B2 * | 11/2020 | Migneco | B60W 50/14 |
| 2003/0120139 | A1 * | 6/2003 | Duval | A61B 5/18 |
| | | | | 600/363 |
| 2003/0151516 | A1 * | 8/2003 | Basir | G08B 21/06 |
| | | | | 340/575 |
| 2006/0042851 | A1 * | 3/2006 | Herrmann | B60R 21/01552 |
| | | | | 180/271 |
| 2008/0266552 | A1 * | 10/2008 | Malawey | G08B 21/06 |
| | | | | 356/138 |
| 2008/0276191 | A1 * | 11/2008 | Breed | B60N 2/002 |
| | | | | 715/771 |
| 2011/0313259 | A1 * | 12/2011 | Hatakeyama | B60K 28/06 |
| | | | | 600/300 |
| 2012/0040665 | A1 * | 2/2012 | Liu | H04W 4/029 |
| | | | | 455/426.1 |
| 2012/0071151 | A1 * | 3/2012 | Abramson | H04W 64/006 |
| | | | | 455/418 |
| 2013/0021153 | A1 * | 1/2013 | Keays | G01N 33/497 |
| | | | | 340/539.12 |
| 2013/0046562 | A1 * | 2/2013 | Taylor | G06Q 40/00 |
| | | | | 705/4 |
| 2013/0150004 | A1 * | 6/2013 | Rosen | H04W 48/04 |
| | | | | 455/414.1 |
| 2013/0175108 | A1 * | 7/2013 | Sultan | B60K 28/066 |
| | | | | 180/272 |
| 2013/0335401 | A1 * | 12/2013 | Beckmann | G01C 21/36 |
| | | | | 345/418 |
| 2014/0055569 | A1 * | 2/2014 | Jeon | A61B 5/18 |
| | | | | 348/47 |
| 2015/0158494 | A1 * | 6/2015 | Lee | B60W 40/08 |
| | | | | 324/671 |
| 2015/0193664 | A1 * | 7/2015 | Marti | A61B 5/18 |
| | | | | 382/103 |
| 2015/0345981 | A1 * | 12/2015 | Goldman-Shenhar | |
| | | | | G01C 21/3602 |
| | | | | 701/533 |
| 2016/0046298 | A1 * | 2/2016 | DeRuyck | B60W 50/14 |
| | | | | 340/576 |
| 2016/0152233 | A1 * | 6/2016 | Fung | G06F 17/00 |
| | | | | 701/41 |
| 2017/0101006 | A1 * | 4/2017 | DeVries | B60W 30/18 |
| 2017/0150360 | A1 * | 5/2017 | Caldwell | H04W 12/082 |

OTHER PUBLICATIONS

Dhawan; *A Warning System Based on Sensor Technology and Chemical Analysis to Detect Distracted Driving*; Presentation for Signature School, Evansville, IN; 2016.
National Highway Traffic Safety Administration (NHTSA) Data—Crash Stats; website visited Sep. 6, 2016; http://www.nhtsa.gov/NCSA>.
French et al.; *Decision-making style, driving style, and self-reported involvement in road traffic accidents*; Ergonomics, 1993, pp. 627-644; vol. 36, No. 6.
YouTube; Arjun Dhawan; JSHS 2016 Submission; *A Warning System Based on Sensor Technology and Chemical Analysis to Detect Distracted Driving* https://www.youtube.com/watch?v=dZrzvPVnJrA&feature=youtu.be.
*Distracted Driving and Crash Risk*; The New England Journal of Medicine; Apr. 17, 2014; pp. 1564-1566; vol. 370, No. 16.
*Distracted Driving 2013*; U.S. Department of Transportation; National Highway Traffic Safety Administration; Apr. 2015.
*Distracted Driving*; Centers for Disease Control and Prevention; website visited Sep. 6, 2016; https://www.cdc.gov/motorvehiclesafety/distracted_driving/>.
*Distracted Driving*; AAA Foundation for Traffic Safety; website visited Oct. 25, 2016; https://www.aaafoundation.org/distracted-driving.
*Distracted Driving Laws*; State Distracted Driving Driving Laws; Sep. 2016; website visited Sep. 6, 2016; http://www.ghsa.org/html/stateinfo/laws/cellphone_laws.html>.
*Distracted Driving: One Call Can Change Everything*; National Safety Council; website visited Sep. 6, 2016; http://www.nsc.org/learn/NSC-Initiatives/Pages/distracted-driving.aspx?var=mnm.
*Distracted Driving Raises Crash Risk*; National Institutes of Health (NIH); Jan. 13, 2014; website visited Sep. 6, 2016; https://www.nih.gov/news-events/nih-research-matters/distracted-driving-raises-crash-risk.
*Drugs and Human Performance Fact Sheets—Cannabis/Marijuana* ($\Delta^9$-Tetrahydrocannabinol, THC); National Highway Traffic Safety Administration; website visited Sep. 6, 2016; http://www.nhtsa.gov/people/injury/research/job185drugs/cannabis.html>.
*Impaired Driving: Get the Facts*; Centers for Disease Control and Prevention; website visited Sep. 6, 2016; http://www.cdc.gov/motorvehiclesafety/impaired_driving/impaired-drv_factsheet.html>.
*Distracted Driving: Facts and Statistics*; Distraction.gov—Official US Government Website for Distracted Driving; website visited Sep. 6, 2016; http://www.distraction.gov/stats-research-laws/facts-and-statistics.html>.
French; *Ford Working on System to Eliminate Distracted Driving*; Lebanon Ford; Jul. 5, 2012; website visited Sep. 6, 2016; http://ford-life.com/2012/07/05/ford-working-on-system-to-eliminate-distracted-drivingt>.
Harbluk et al.; *The Impact of Cognitive Distraction on Driver Visual Behaviour and Vehicle Control*; Feb. 2002; Transport Canada; website visited Sep. 6, 2016; https://trid.trb.org/view.aspx?id=643031>.
*Measuring Cognitive Distractions*; AAA Foundation for Traffic Safety; website visited Sep. 6, 2016; https://www.aaafoundation.org/measuring-cognitive-distractions>.
*New NIDA Study: THC Blood Levels Do Not Accurately Measure Intoxication*; The Joint Blog; Feb. 2014; website visited Sep. 6, 2016; http://thejointblog.com/new-nida-study-thc-blood-levels-accurately-measure-intoxication/>.
Donmez et al.; *Safety implications of providing real-time feedback to distracted drivers*; Accident Analysis & Prevention; May 2007; pp. 581-590; vol. 39, Issue 3; Abstract only from Science Direct; website visited Sep. 6, 2016;. http://www.sciencedirect.com/science/article/pii/S0001457506001783.
*Self-driving cars: The next revolution*; KPMG and the Center for Automotive Research (CAR);. 2012; http://www.kpmg.com/US/en/IssuesAndInsights/ArticlesPublications/Documents/self-driving-cars-next-revolution.pdf>.
Bramlet; *10 Deadliest Driving Distractions*; PropertyCasualty360; Apr. 11, 2013; website visited Sep. 6, 2016; http://propertycasualty360.com/2013/04/11/10-deadliest-driving-distractions?page_all=1>.
Carson; *Toyota is using Oculus Rift to educate drivers about distracted driving*; Tech Republic; Feb. 16, 2015; website visited Sep. 6, 2016; http://www.techrepublic.com/article/toyota-is-using-oculus-rift-to-educate-drivers-about-distracted-driving/>.
Young et al.; *Driver distraction: A review of the literature*; Distracted driving;. Australasian College of Road Safety; 2007; pp. 379-405.

(56) References Cited

OTHER PUBLICATIONS

*What does x, y, z values obtained from accelerometer in Android indicate?*; Stack Overflow;. website visited Sep. 6, 2016; http://stackoverflow.com/questions/23871599/what-does-x-y-z-values-obtained-from-accelerometer-in-android-indicate>.

*Distracted driving*; Insurance Institute for Highway Safety/ Highway Loss Data Institute; website. visited Sep. 6, 2016; http://www.iihs.org/iihs/topics/t/distracted-driving/topicoverview.

Salamon; *Who are those distracted teen drivers calling and testing? Often, mom or dad*; Health Day; Aug. 8, 2014; CBS News; website visited Sep. 6, 2016;. http://www.cbsnews.com/news/distracted-teen-drivers-often-on-cellphone-or-texting-with-parent/.

*2014 Distracted Driving Awareness Month—Key Facts & Statistics*; California Office of Traffic Safety; website visited Sep. 6, 2016; http://www.ots.ca.gov/pdf/campaign/2014_distracted_driving_fact_sheet.pdf.

*Distracted Driving*; Insurance Information Institute; website visited Sep. 6, 2016; http://www.iii.org/article/distracted-driving.

*Cannabis (drug)—Pharmacology—Mechanism of action*; Wikipedia; website visited Oct. 25, 2016; https://en.wikipedia.org/wiki/Cannabis_(drug)#Mechanism_of_action.

O'Toole; *Apple's CarPlay draws safety criticism*; Mar. 5, 2014; CNN Money; website visited Sep. 6, 2016; http://money.cnn.com/2014/03/05/technology/mobile/apple-carplay/.

*A growing problem of driver distraction*; World Health Organization; website visited Sep. 6, 2016; http://www.who.int/violence_injury_prevention/publication/road_traffic/distracted_driving_summary.pdf.

McEvoy et al.; *The impact of driver distraction on road safety: results from a representative survey in two Australian states*; Injury Prevention; Aug. 2006; pp. 242-247; vol. 12, No. 4; website visited Oct. 25, 2016; https://www.ncbi.nlm.gov/pmc/articles/PMC2586781/.

Beirness; *Distracted Driving: The Role of Survey Research*; website visited Oct. 25, 2016; http://www.distracteddriving.ca/english/documents/DougBeirness_000.pdf.

\* cited by examiner

DRIVER FOCUS ANALYZER

CROSS REFERENCE TO RELATED APPLICATIONS

This application is a continuation of U.S. application Ser. No. 15/257,153 filed on Sep. 6, 2016, entitled "Driver Focus Analyzer", which claims the benefit of U.S. Provisional Application No. 62/281,835 filed on Jan. 22, 2016, entitled "Warning System Based on Sensor Technology and Chemical Analysis to Detect Distracted Driving", the entire contents of each being incorporated herein by reference in their entireties.

TECHNICAL FIELD

Example embodiments generally relate to vehicle safety systems and, in particular, relate to a driver focus analyzer.

BACKGROUND

Over 1,100 people in the U.S. are either injured or die from distracted driving crashes every day. Distractions can be visual, manual, or cognitive. Current safety devices are based on reducing collisions through sensors configured to sense conditions exterior to a vehicle, e.g. distance to car ahead, blind spot indicator, reversing camera, parking sonar, or the like.

Approximately ten percent of fatal crashes, eighteen percent of injury crashes, and sixteen percent of all motor vehicle crashes are reported as distraction-affected crashes, including manual distractions, (e.g. taking hands off of a steering wheel), visual distractions (e.g. taking eyes off of the road), cognitive distraction (taking mind off of the drive), or a combination thereof. Distracted driving has gained significant attention recently as electronic devices in vehicles become more prevalent. However, non technological distractions also remain, such as conversations with passengers, drowsiness, noise in the vehicle (e.g. kids distracting the drivers), eating, putting on makeup, alcohol, drugs (e.g. marijuana), or the like.

BRIEF SUMMARY OF SOME EXAMPLES

Accordingly, some example embodiments may enable a driver focus analyzer including one or more sensors configured to measure a distance of a driver or computing device from the one or more sensors, processing circuitry configured to compare the distance to a predetermined distance threshold, determine if the distance exceeds the predetermined distance threshold, and cause an alert in response to at least determining that the distance exceeds the predetermined threshold, and an alert output device configured to generate an audio or visual output in response to the alert.

In an example embodiment a driver focus analyzer is provided including one or more sensors configured to measure an intoxicant level proximate to the driver, processing circuitry configured to compare the intoxicant level to a predetermined intoxicant threshold, determine if the intoxicant level exceeds the predetermined intoxicant threshold, and cause an alert in response to determining that the intoxicant level exceeds the predetermined threshold, and an alert output configured to generate an audio or visual output in response to the alert.

In another example embodiment a driver focus analyzer is provided including one or more sensors configured to measure a noise level proximate to the driver, processing circuitry configured to compare the noise level to a predetermined noise threshold, determine if the noise level exceeds the predetermined noise threshold, and cause an alert in response to determining that the noise level exceeds the predetermined threshold, and an alert output configured to generate an audio or visual output in response to the alert.

BRIEF DESCRIPTION OF THE SEVERAL VIEWS OF THE DRAWING(S)

Having thus described the driver focus analyzer in general terms, reference will now be made to the accompanying drawings, which are not necessarily drawn to scale, and wherein:

DETAILED DESCRIPTION

Figure 1:
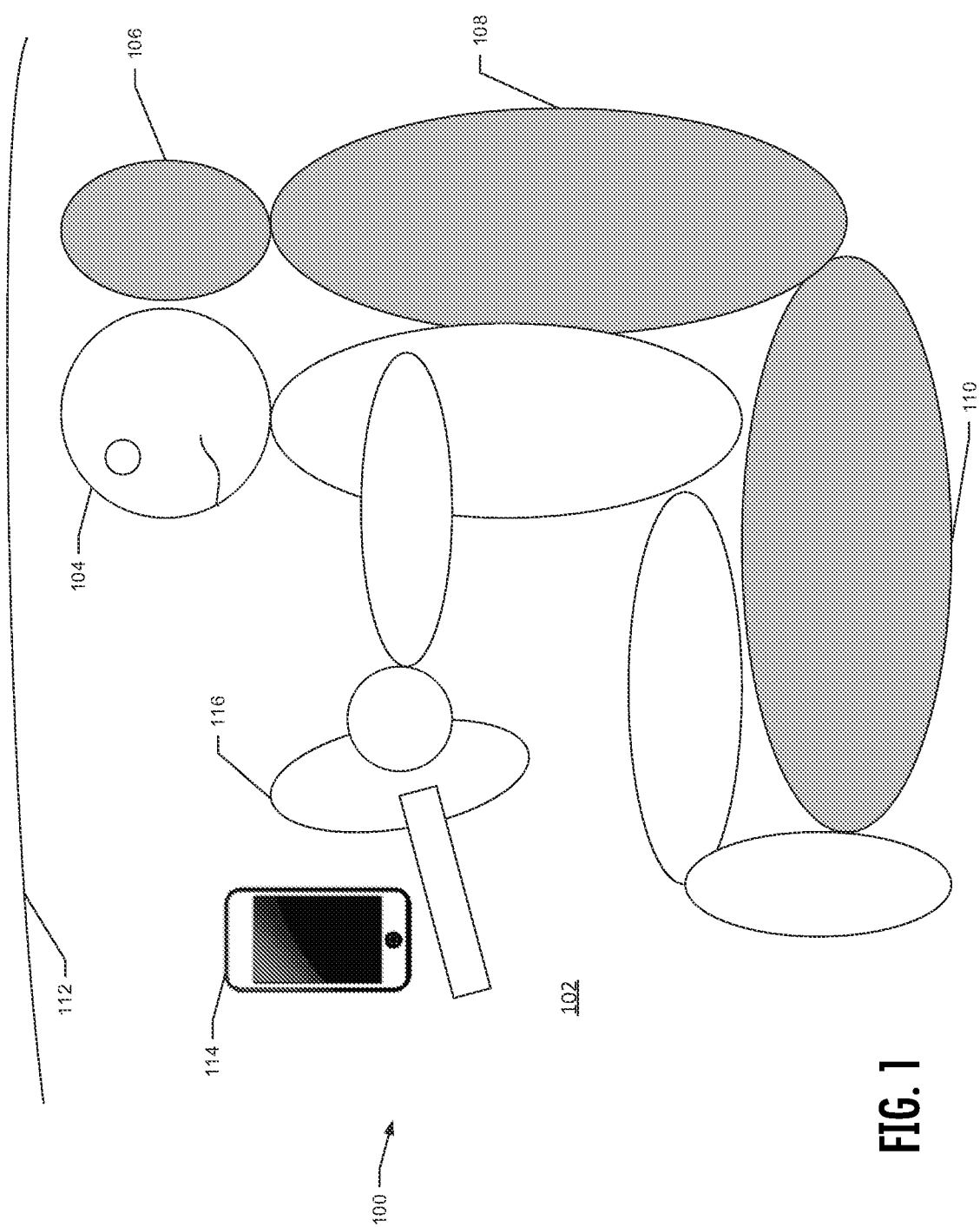
FIG. 1 illustrates an example driver in a vehicle seat according to example embodiments of the present invention described herein.

Some example embodiments now will be described more fully hereinafter with reference to the accompanying drawings, in which some, but not all example embodiments are shown. Indeed, the examples described and pictured herein should not be construed as being limiting as to the scope, applicability or configuration of the present disclosure. Rather, these example embodiments are provided so that this disclosure will satisfy applicable legal requirements. Like reference numerals refer to like elements throughout. As used herein, operable coupling should be understood to relate to direct or indirect connection that, in either case, enables functional interconnection of components that are operably coupled to each other.

In an example embodiment, a driver focus analyzer is provided including a plurality of sensors, processing circuitry, and an alert output device. Each of the sensors is associated with a particular type of driver distraction, such as proximity sensors for sensing if the driver is watching the road or if a computing device (e.g., a cell phone or smart phone) is moving toward the driver, noise sensors for sensing high noise levels in a vehicle, and/or intoxicant sensors for detecting intoxicant levels of alcohol, tetrahydrocannabinol (THC), or the like.

The processing circuitry may be configured to receive sensor data from each of the sensors and determine if the sensor data satisfies a predetermined threshold, e.g. high noise level, distance indicative of eyes not oriented toward the road, high intoxication level, or the like.

In an instance in which the driver focus analyzer determines that a predetermined threshold is satisfied the processing circuitry may cause an alert to be generated. An alert output, such as a light, buzzer, or speaker, may provide an audio or visual cue to the driver and/or passengers that the predetermined threshold has been satisfied. The audio or visual cue may cause the driver and/or passengers to take actions to place the vehicle in a safer condition (e.g., turn down the radio, stop yelling, direct the driver's attention back to the road, not operate the vehicle, etc.).

FIG. 1 illustrates an example system 100 including a driver focus analyzer deployed in a vehicle 102 according to an example embodiment. The vehicle 102 may be any vehicle operated by a driver 104, such as a car, truck, construction equipment, airplane, boat, or the like. The vehicle 102 may have a field of view for the driver 104 for safe operations, such as a windshield of a boat, airplane, car, or the like. It may be advantageous to ensure that the driver is monitoring the field of view for safe operations during the operation of the vehicle 102. The driver 102 may look away from the field of view for safe operations due to any number of distractions, such as reading signs or looking at an accident, drowsiness, looking at a computing device 114, or the like. Additionally, it may be advantageous to monitor that the noise levels in the vehicle 102 are with a range to not distract the driver 104 and/or ensure that the driver 104 is not intoxicated during the operation of the vehicle 102.

To monitor the driver and/or conditions associated with the driver 104, the vehicle may include a driver focus analyzer, as discussed below in FIG. 2. The driver focus analyzer may be disposed in a portion of a driver's seat of the vehicle 102, for example the head rest 106, seat back 108, seat cushion 110, armrests, or the like. Additionally or alternatively, the driver focus analyzer may be disposed in a portion of the cabin, such as a head liner 112.

Figure 2:
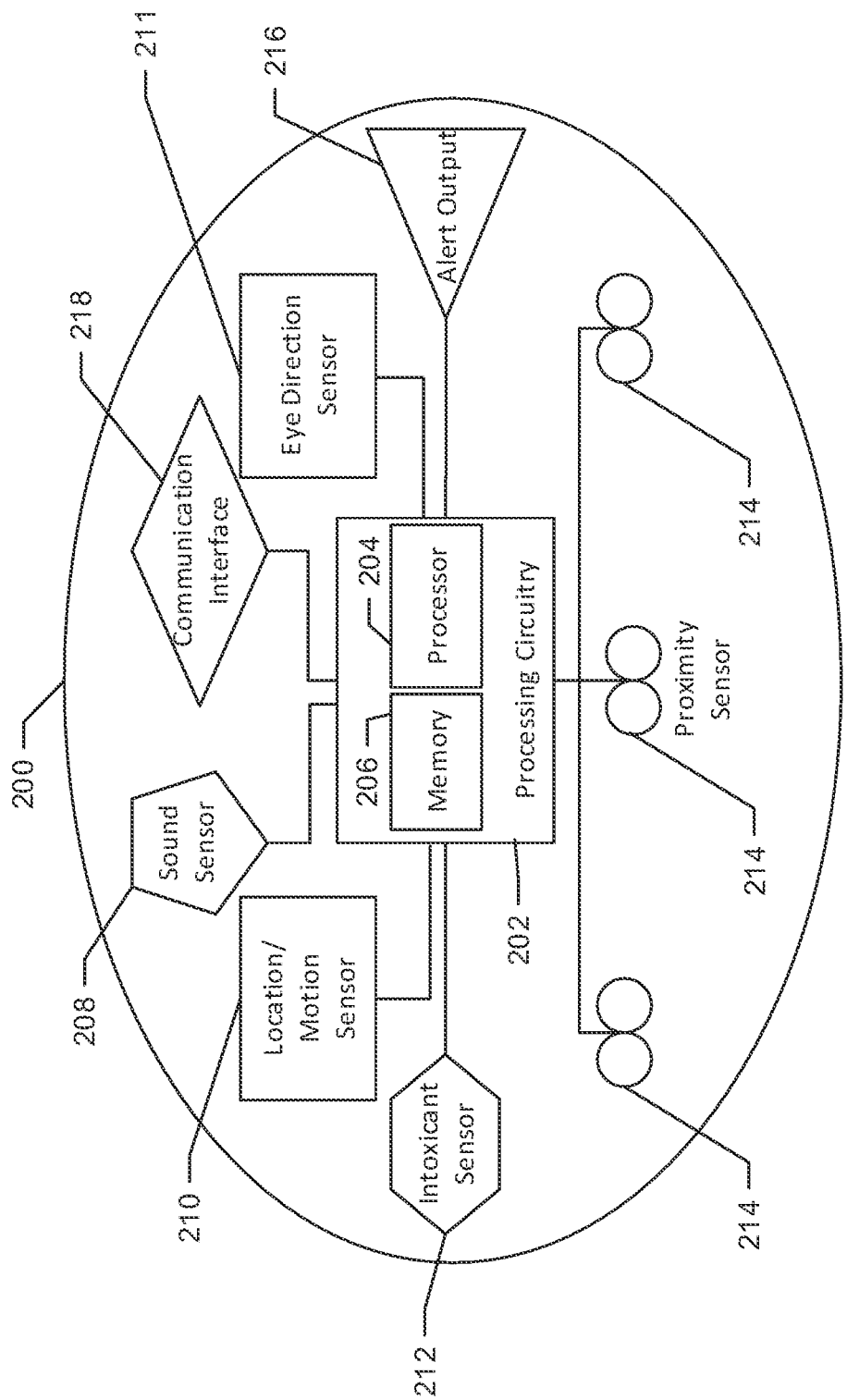
FIG. 2 illustrates an example driver focus analyzer according to example embodiments of the present invention described herein.

FIG. 2 illustrates an example driver focus analyzer according to an example embodiment. In an example embodiment, the driver focus analyzer is disposed in a vehicle headrest 200, but may be disposed in one or more components of driver's seat or the cabin of the vehicle, such as vehicle 102 as discussed above in FIG. 1. The driver focus analyzer may include or otherwise be in communication with processing circuitry 202 that is configured to perform data processing, application execution and other processing and management services according to an example embodiment. In one embodiment, the processing circuitry 202 may include a memory 206 and a processor 204 that may be in communication with or otherwise control an alert output 216 and a communication interface 218. As such, the processing circuitry 202 may be embodied as a circuit chip (e.g. an integrated circuit chip) configured (e.g. with hardware, software or a combination of hardware and software) to perform operations described herein. However, in some embodiments, the processing circuitry 202 may be embodied as a portion of a one of various mobile computing devices or wearable computing devices.

The alert output 216 may include one or more lighting elements and/or audio elements. The lighting elements may include light emitting diodes (LEDs), incandescent bulbs, florescent lights, or the like. The audio elements may include a buzzer, a speaker, or the like. The alert output 216 may cause the lighting elements and/or audio elements to actuate, such as flash, or alarm, in an instance in which the processing circuitry 202 causes an alert, as described below.

The communication interface 218 may be any means such as a device or circuitry embodied in either hardware, software, or a combination of hardware and software that is configured to receive and/or transmit data from/to a network and/or any other device or module in communication with the driver focus analyzer. The communication interface 218 may also include, for example, an antenna (or multiple antennas) and supporting hardware and/or software for enabling communications with a network or other devices (e.g. a computing device 114). In some environments, the communication interface 218 may alternatively or additionally support wired communication. As such, for example, the communication interface 218 may include a hardware/software for supporting communication via cable, universal serial bus (USB), or other mechanisms. In an exemplary embodiment, the communication interface 218 may support communication via one or more different communication protocols or methods. In some cases, IEEE 802.15.4 based communication techniques such as ZigBee, BlueTooth, or other low power, short range communication protocols, such as a proprietary technique based on IEEE 802.15.4 may be employed along with radio frequency identification (RFID) or other short range communication techniques. In other embodiments, communication protocols based on the draft IEEE 802.15.4a standard may be established.

In an example embodiment, the memory 206 may include one or more non-transitory storage or memory devices such as, for example, volatile and/or non-volatile memory that may be either fixed or removable. The memory 206 may be configured to store information, data, applications, instructions or the like for enabling the apparatus to carry out various functions in accordance with example embodiments of the present invention. For example, the memory 206 could be configured to buffer input data for processing by the processor 204. Additionally or alternatively, the memory 206 could be configured to store instructions for execution by the processor 204. Among the contents of the memory 206, applications may be stored for execution by the processor 204 in order to carry out the functionality associated with each respective application.

The processor 204 may be embodied in a number of different ways. For example, the processor 204 may be embodied as various processing means such as a microprocessor or other processing element, a coprocessor, a controller or various other computing or processing devices including integrated circuits such as, for example, an ASIC (application specific integrated circuit), an FPGA (field programmable gate array), a hardware accelerator, or the like. In an example embodiment, the processor 204 may be configured to execute instructions stored in the memory 206 or otherwise accessible to the processor 204. As such, whether configured by hardware or software methods, or by a combination thereof, the processor 204 may represent an entity (e.g. physically embodied in circuitry) capable of performing operations according to embodiments of the present invention while configured accordingly. Thus, for example, when the processor 204 is embodied as an ASIC, FPGA or the like, the processor 204 may be specifically configured hardware for conducting the operations described herein. Alternatively, as another example, when the processor 204 is embodied as an executor of software instructions, the instructions may specifically configure the processor 204 to perform the operations described herein.

In some embodiments, the processing circuitry 202 may be in communication with a sound sensor 208. The sound sensor may be a sound or vibration sensor, such as a dynamic, electrostatic, or condenser microphone; a piezoelectric sensor, or the like. The microphone may be positioned in the cabin of the vehicle 102, such that the microphone detects the ambient noise in the cabin. In an example embodiment, the microphone may be a dedicated microphone for the driver focus analyzer. In some example embodiments, the microphone may be a vehicle microphone for hands free communication, or a microphone associated with a computing device 114. In some example embodiments, the microphone may be positioned proximate to the driver 104, to sense the ambient noise level proximate to the driver 104, for example in the head rest 200.

In an example embodiment, the processing circuitry 202 may be in communication with one or more location/motion sensors 210. The location/motion sensors 210 may sense the location of at least a portion of the driver focus analyzer such as the portion disposed in the head rest 200. The location may be based on a global positioning system (GPS) signals, a RFID beacon, or the like. Additionally or alternatively, the location/motion sensor 210 may sense motion associated with the driver focus analyzer, e.g. the portion in the head rest 200. The motion sensing may be based on accelerometer measurements, gyroscopes, or the like. In other example embodiments, the location/motion sensor 210 may include one or more pressure sensors, such as disposed in the seat bask or seat cushion, which may sense a shift in weight of the driver 104, such as leaning forward (e.g. picking something up) or shifting to one side (e.g. removing a wallet from a back pocket.)

In some example embodiments, the processing circuitry 202 may be in communication with one or more intoxicant sensors 212. The intoxicant sensors 212 may be configured to sense an intoxicant level in the cabin of the vehicle 102. In some embodiments, the intoxicant sensors 212 may be disposed proximate to the driver 104 to sense the intoxicant level proximate to the driver 104. The intoxicant sensors 212 may be configured to sense the intoxicant level of one or more different types of intoxicants, such as alcohol, THC, or the like. In some example embodiments, the intoxicant sensors 210 may include a gas sensor, such as a MQ-3 semiconductor sensor, canna sensor, or the like.

In an example embodiment, the processing circuitry 202 may be in communication with one or more proximity sensors 214. The proximity sensors 214 may be configured to measure a distance of the driver 104 from the proximity sensor 214. The proximity sensors 214 may include electromagnetic sensors, capacitive sensors, photoelectric sensors, pressure sensors, ultrasonic sensors, magnetic sensors, inductive sensors, or the like.

In an instance in which the driver focus analyzer includes an intoxicant sensor 212 configured to detect alcohol, the processing circuitry 202 may compare the airborne alcohol level to a predetermined intoxicant threshold, such as a predetermined alcohol threshold. The airborne alcohol threshold may be based on the legal limit for impaired driving such as 0.08 percent blood alcohol content (BAC). For example, the predetermined alcohol threshold may be set as approximately $2*10^-4$ g/l at the 0.08 BAC limit, $1*10^-4$ g/l at 0.04 BAC, e.g. half the legal limit. These alcohol thresholds are merely illustrative and other limits, either higher or lower, may be used depending on the legal limits or other driver 104 or vehicle 102 specific factors, such as age and weight of the driver 104, or size or ventilation of the cabin of the vehicle 102. In an instance in which the processing circuitry 202 determines that the predetermined alcohol threshold has been satisfied, e.g. exceeded, the processing circuitry 202 may generate an alert. The alert output 216 may cause an audio or visual indication that a driver focus threshold has been satisfied, which may in turn alert the driver 104 and/or passengers that the driver 104 may be impaired by alcohol and should not drive the vehicle 102.

In an example embodiment in which the driver focus analyzer includes an intoxicant sensor 212 configured to detect THC, the processing circuitry 202 may be configured to compare a sensed airborne THC level to a predetermined intoxicant threshold, such as a predetermined THC threshold. The predetermined THC threshold may be based on the airborne discharge from a marijuana cigarette. Approximately half of an expected amount of THC of a marijuana cigarette, e.g. approximately 24 mg, may be discharged to air, e.g. 12 mg. The airborne THC may be expected to evenly distribute about the cabin of the vehicle 102. The predetermined THC threshold may be the airborne THC divided by the cabin volume. For example, if the cabin of the vehicle, such as a van, is 79281, the predetermined THC threshold may be $1.5*10^-6$ g/l. In an instance in which the processing circuitry 202 determines that the predetermine THC threshold has been satisfied, e.g. exceeded, the processing circuitry 202 may generate an alert. The alert output 216 may cause an audio or visual indication that a driver focus threshold has been satisfied, which may, in turn, alert the driver and/or passengers that the driver may be impaired by THC and should not drive.

In some example embodiments in which the drive focus analyzer includes a sound sensor, the processing circuitry 202 may compare the sensed noise level in the cabin of the vehicle 102 to a predetermined noise threshold. The predetermined noise threshold may be based on a noise level which may be distracting to the driver such as 50 dB, 60 dB, or the like, or in some instances the predetermined noise threshold may be based on noise levels which may be damaging to the hearing of the driver and/or passengers, such as 85 dB. In an instance in which the processing circuitry 202 determines that the predetermine noise threshold has been satisfied, e.g. exceeded, the processing circuitry 202 may generate an alert. The alert output 216 may cause an audio or visual indication that a driver focus threshold has been satisfied, which may, in turn, alert the driver and/or passengers that the noise level is distracting to the driver and/or may be causing damage to the driver and/or passenger's hearing.

In an example embodiment in which the driver focus analyzer includes one or more proximity sensors 214, the processing circuitry 202 may compare the measured distance of the driver from the proximity sensor 214 to one or more predetermined distance thresholds, such as a predetermined position threshold. The predetermined position thresholds may include a distance from the proximity detectors 214 indicating the driver is not sitting back in the seat, e.g. leaning forward to pick something up or to change the radio station. In some examples, the predetermined position threshold may be based on two or more proximity detector 214 measurements, for example two or more proximity sensors 214 disposed in the headrest 200. The predetermined position threshold may be based on the head of the driver 104 being turned away from the field of view for safe operation of the vehicle 102, such as a left sensor measuring a distance of greater than 4 cm while a right and/or center sensor measure a distance of less than 4 cm, which may be indicative of the driver's head being turned substantially toward the right. In an instance in which the processing circuitry 202 determines that the predetermined position threshold has been satisfied, e.g. exceeded, the processing circuitry 202 may generate an alert. The alert output 216 may cause an audio or visual indication that the predetermined position threshold has been satisfied, which may, in turn, alert the driver and/or passengers that the driver 104 may not be looking at the field of view for safe operation of the vehicle 102.

In some example embodiments, a cover, such as a head rest cover may alter the measured distance. For example, in an instance in which the proximity 314 sensor is an ultrasonic sensor, the measured value may indicate a value larger than true distance. In some instances the difference between the true distance and the measured distance may be a linear divergence. The processing circuitry 202 may be further configured to correct the measured distance, such as by multiplying the measured value by a linear divergence factor, such as 0.9963. The linear divergence factor may be determined for the specific proximity sensor 314 and cover material, by factory testing.

In some example embodiments, the predetermined position threshold may also include a predetermined time value, such as 2 seconds, 5 seconds, 2 sensor readings, 5 sensor reading, or the like. The predetermined time value may account for the driver adjusting position, performing a blind spot check, looking briefly at signs or address information or the like. The alert may be generated or caused in an instance in which the position threshold is satisfied for the predetermined time value.

In an example embodiment in which the driver focus analyzer includes a location/motion sensor 210, the processing circuitry 202 may compare the sensed location or motion data to a predetermined distance threshold, such as a predetermined motion threshold. In an example embodiment, the location/motion sensor 210 may include one or more pressure sensors in the seat back or seat cushion. The location/motion sensor 210 may sense a change in pressure in one or more of the pressure sensors indicative of the driver 104 leaning forward to one side. The indication of the driver 104 not being properly seated in the seat may be indicative of the driver not looking at the field of view for safe operations for the vehicle 102. The motion threshold in this example may be a deviation, such as 4 kg, 5, kg, or the like between sensors, or from an average pressure. In an instance in which the processing circuitry 202 determines that the predetermined motion threshold has been satisfied, e.g. exceeded, the processing circuitry 202 may generate an alert. The alert output 216 may cause an audio or visual indication that the predetermined motion threshold has been satisfied, which may, in turn, alert the driver and/or passengers that the driver may not be looking at the field of view for safe operation of the vehicle.

In some example embodiments, the driver focus analyzer includes an eye direction sensor 211. The eye direction sensor 211, such as an infrared camera, may be integrated into eyewear, such as glasses, or integrated into a dashboard of the vehicle 102. The eye direction sensor 211 may sense a gaze direction of one or both eyes of the driver 104. The processing circuitry 202 may compare the gaze direction to a predetermined threshold, such as a predetermined gaze direction threshold. The eye direction sensor may sense a change gaze direction indicative of the driver 104 not looking at the field of view for safe operations for the vehicle 102. The gaze direction threshold in this example may be a deviation, such as 1 mm, 2 mm, or the like from predetermined center gaze position. In an instance in which the processing circuitry 202 determines that the predetermined gaze direction threshold has been satisfied, e.g. exceeded, the processing circuitry 202 may generate an alert. The alert output 216 may cause an audio or visual indication that the predetermined motion threshold has been satisfied, which may, in turn, alert the driver and/or passengers that the driver may not be looking at the field of view for safe operation of the vehicle.

Additionally or alternatively, a computing device, such as computing device 114 may include or be associated with a location sensor, such as GPS. The processing circuitry 202 may receive location data from a location sensor associated with the computing device 114, through the communications interface 218. The location/motion sensor 210 may provide data indicative of a location of the driver focus analyzer. The processing circuitry 202 may use the location data associated with the computing device 114 to determine a range between the location/motion sensor 210 and the computing device 114. The processing circuitry 202 may also compare the range at a predetermined interval such as 1 second, 10 seconds, 30 seconds, or the like to a predetermined range threshold. The range threshold may be a set value such as 30 cm or a deviation, such as 5 cm, 10 cm, or the like from a starting position or average range. In an instance in which the processing circuitry 202 determines that the predetermined range threshold has been satisfied, e.g. exceeds, the processing circuitry 202 may generate an alert. In some embodiments, the processing circuitry 202 may cause an alert when the range threshold is satisfied for a predetermined number of intervals, such as 2 intervals, 3 intervals, or the like. The alert output 216 may cause an audio or visual indication that the predetermined range threshold has been satisfied, which may, in turn, alert the driver 104 and/or passengers that the driver 104 may be interacting with the computing device 114 and therefore not looking at the field of view for safe operation of the vehicle 102.

In some example embodiments, the computing device 114 may include or be associated with one or more motion sensors, such as accelerometers or gyroscopes. The processing circuitry 202 may receive motion data from the one or more motion sensors associated with the computing device 114, through the communications interface 208. The location/motion sensor 210 may provide data indicative of a motion of the driver focus analyzer. The processing circuitry 202 may use the motion data of the computing device and the driver focus analyzer to determine a relative motion between the computing device 114 and the driver focus analyzer. The motion data may be the difference between the motion data provided by the location/motion sensor 210 and the motion data associated with the computing device 114. For example, if the motion data associated with the computing device 114 and the driver focus analyzer is substantially the same, e.g. no relative motion, the computing device 114 may be stationary, such in on a dash board or in a cup holder. If the motion data associated with the computing device 114 and the driver focus analyzer diverge, the computing device 114 may be in motion such as being picked up and brought nearer to the driver. In some instances the relative motion data may be averaged, such as over 1 second, 5 seconds, 10 sensor readings, 50 sensor readings, 100 sensor readings, or the like. The processing circuitry 202 may compare the relative motion to a predetermined motion threshold such as 5 cm, 10 cm, or the like. In an instance in which the processing circuitry 202 determines that the relative motion satisfies, e.g. exceeds, the predetermined motion threshold, the processing circuitry may cause an alert.

In some embodiments, the relative motion may be indicative of computing device motions, such movement in horizontal direction away or toward the driver focus analyzer, which may be indicative of the computing device 114 sliding on the dash board, or diagonal motion toward the driver focus analyzer, which may be indicative of bringing the computing device 114 near the driver's face. The motion threshold may, in some instances include specific device motions. As such, the relative motion indicative of a sliding computing device 114 may not cause the alert and the relative motion of the computing device nearing the driver's face may cause the alert.

In an example embodiment the motion data associated with the computing device 114 may be user to determine if the vehicle 102 is in motion or stationary. The processing circuitry may be further configured to cause an alert when the vehicle 102 is determined to be in motion and not cause an alert when the vehicle 102 is stationary. Preventing alerts when the vehicle 102 is stationary may reduce instances of alerts which do not contribute to increased safety, e.g. false positives.

Figure 3:
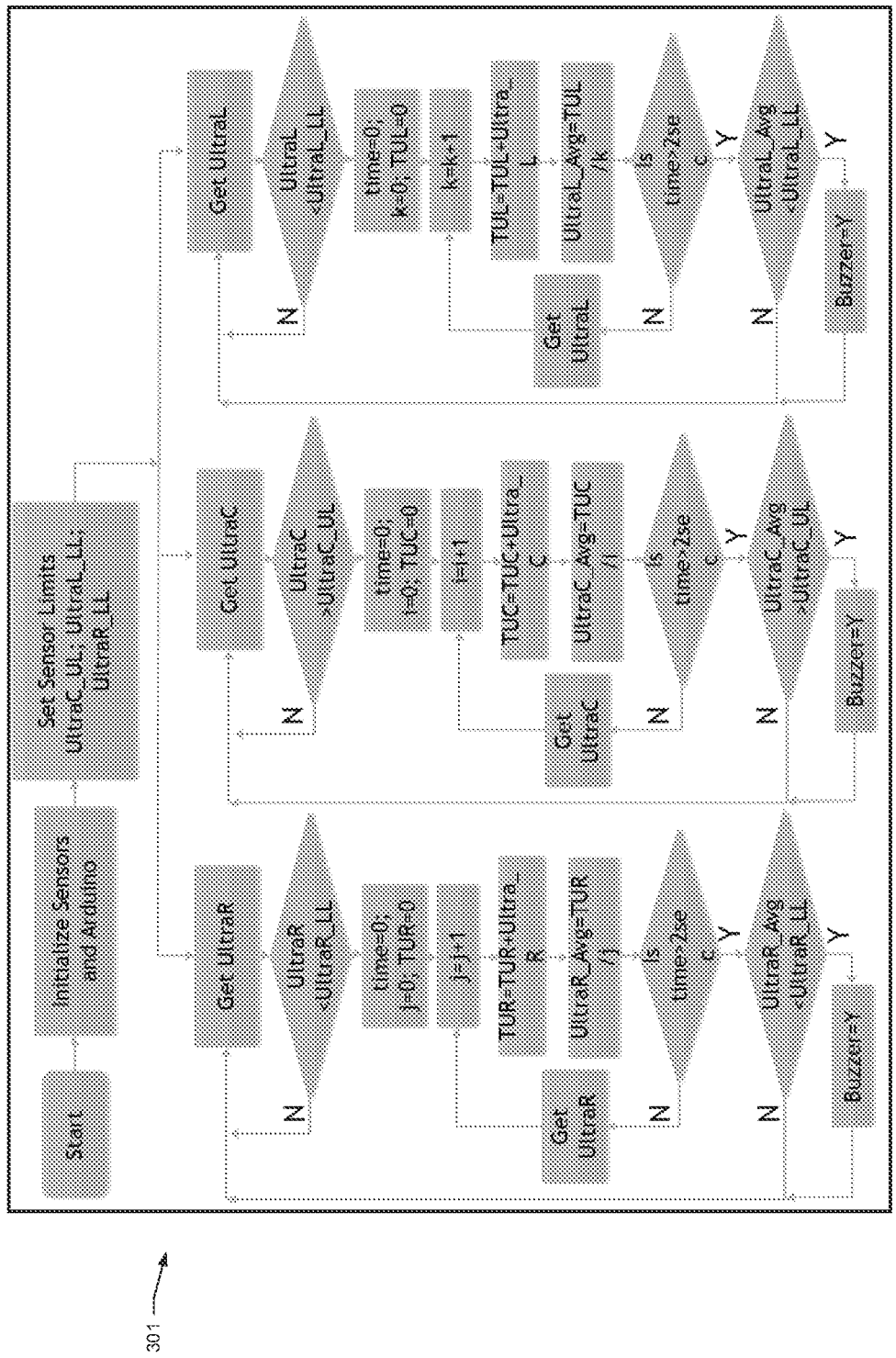
FIG. 3 illustrates an example proximity sensor flowchart according to example embodiments of the present invention described herein.

FIG. 3 illustrates a software program 301 for causing the proximity sensors (left (L), right (R), and center (C)) to measure the distance of the driver 104 from the proximity sensors 214. The program 300 compares the proximity data Ultra_x to the predetermined distance threshold TUx at a 2 second interval. The program additionally compares the average sensor reading Ulta x_Avg to set sensor limits Ultrax_LL and UltraC_UL, indicative of proper sensor operation. In an instance in which the sensor data exceeds the predetermined distance threshold, the program may cause an alert (Buzzer=Y). Similarly, in an instance in which the average sensor data exceeds the set sensor limit, the program 300 may cause the alert.

Figure 4:
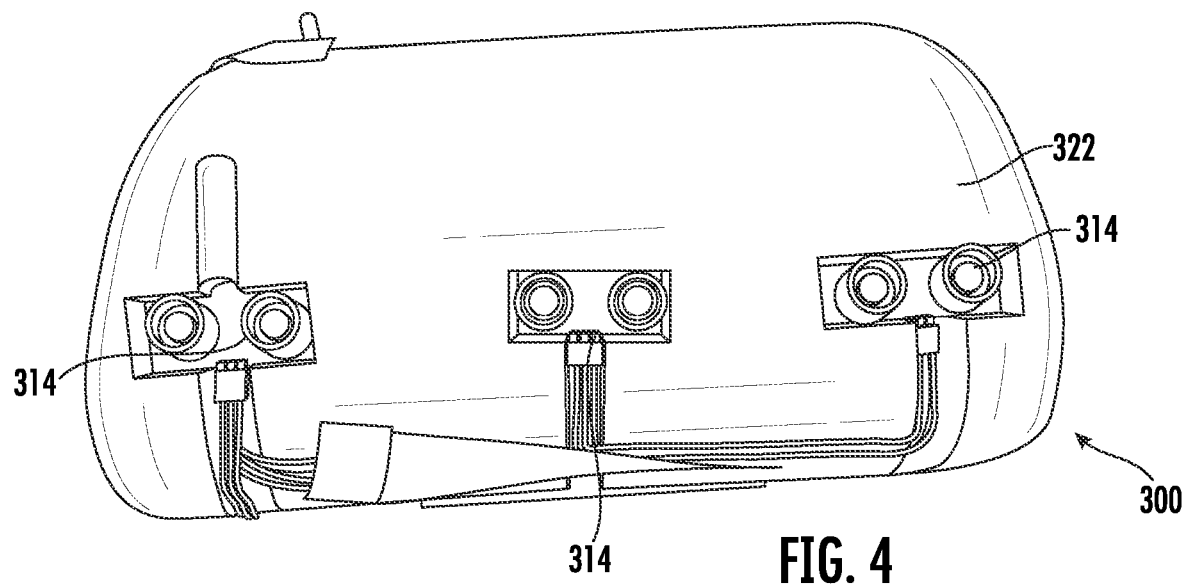
FIGS. 4-7 illustrate an example driver focus analyzer disposed in a vehicle head rest according to example embodiments of the present invention described herein.

FIG. 4 illustrates a front view of a head rest 300 according to an example embodiment. Proximity sensors 314 may be disposed in recesses in foam or padding of the head rest 300, such as in the front of the head rest 300.

Figure 5:
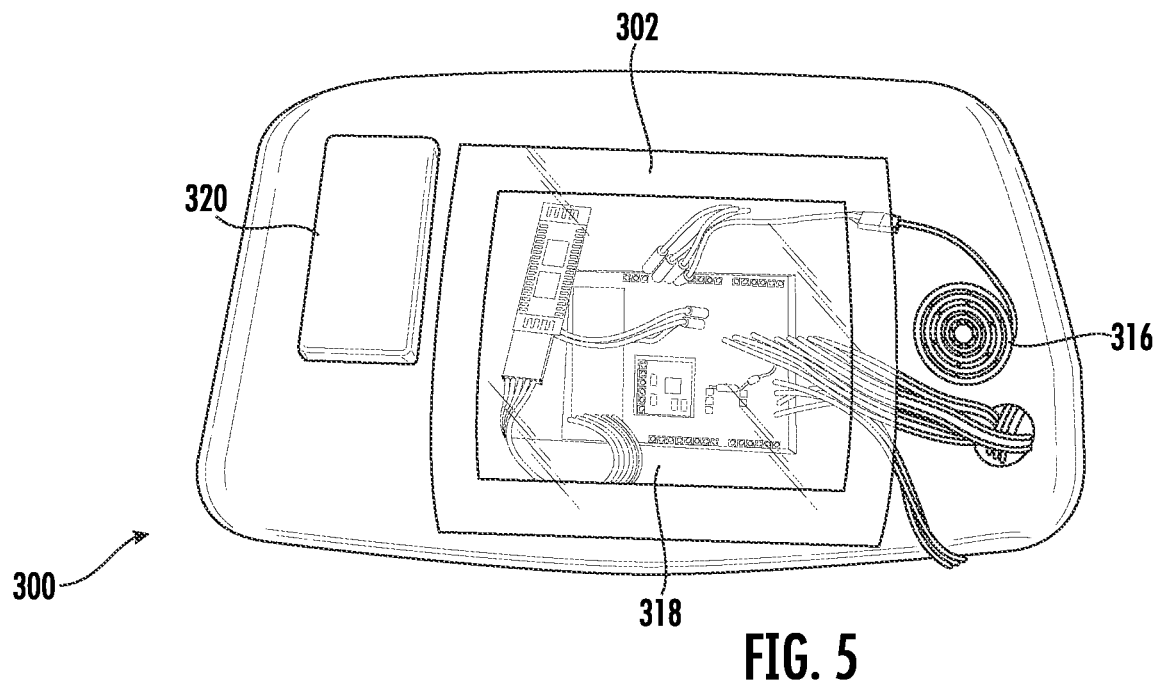

FIG. 5 illustrates a back view of the head rest 300, according to an example embodiment. Processing circuitry 302, a communications interface 318, and/or an alert output 316 may be disposed in a recess in the foam or padding of the head rest 300, such as in the back of the head rest 300. In some example embodiments, a stand alone or back up power supply 320 for the driver focus analyzer may also be disposed in the foam or padding of the head rest 300.

Figure 6:
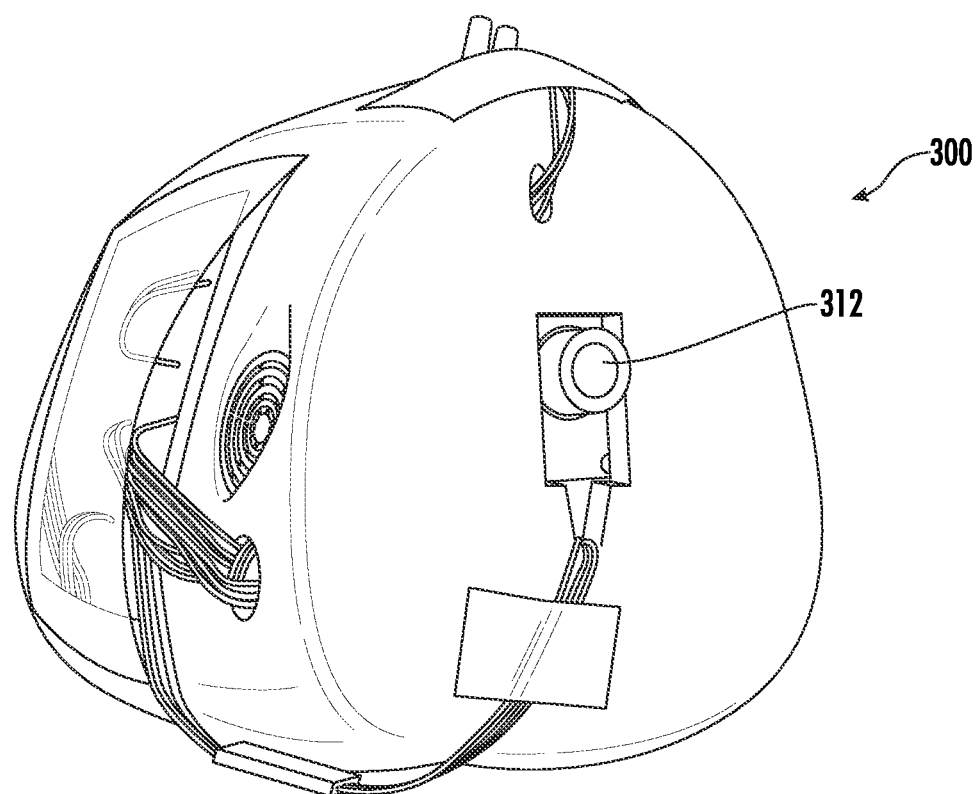

FIG. 6 illustrates a left side view of the head rest 300 according to an example embodiment. An intoxicant sensor 312 may be disposed in the foam or padding of the head rest 300, such as in the right side of the head rest 300.

Figure 7:
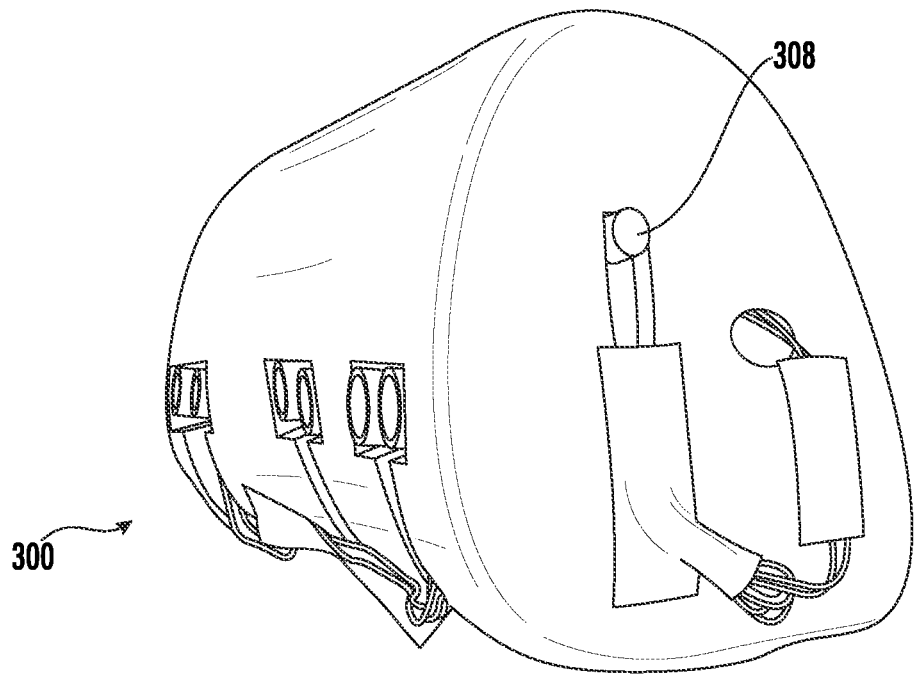
Figure 8:
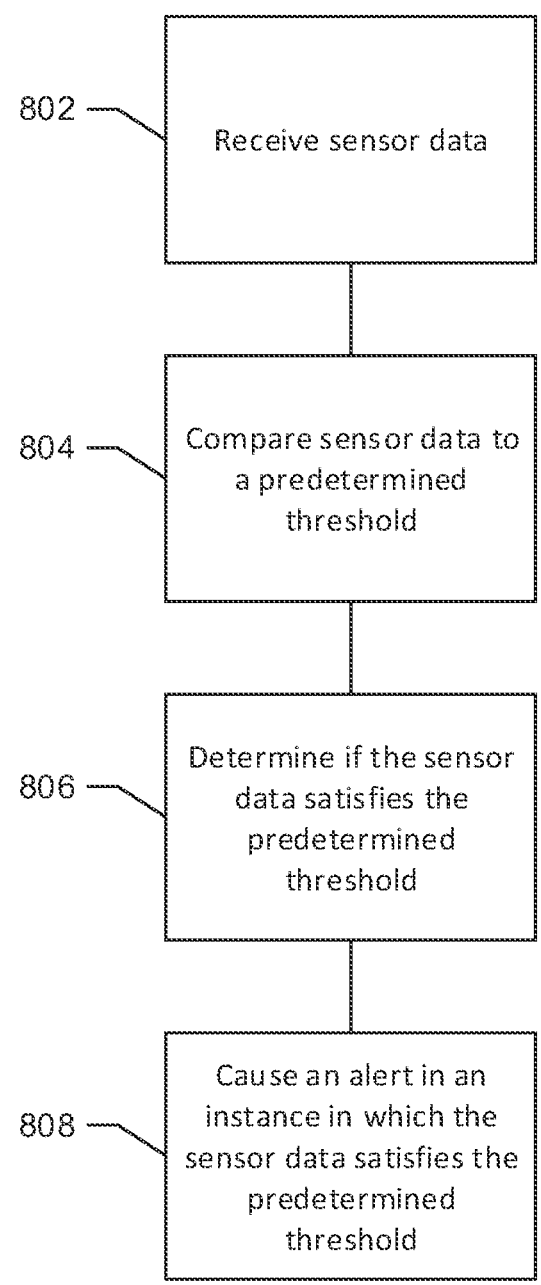
FIGS. 8-11 illustrate example methods of utilizing a driver focus analyzer according to example embodiments of the present invention described herein.
Figure 9:
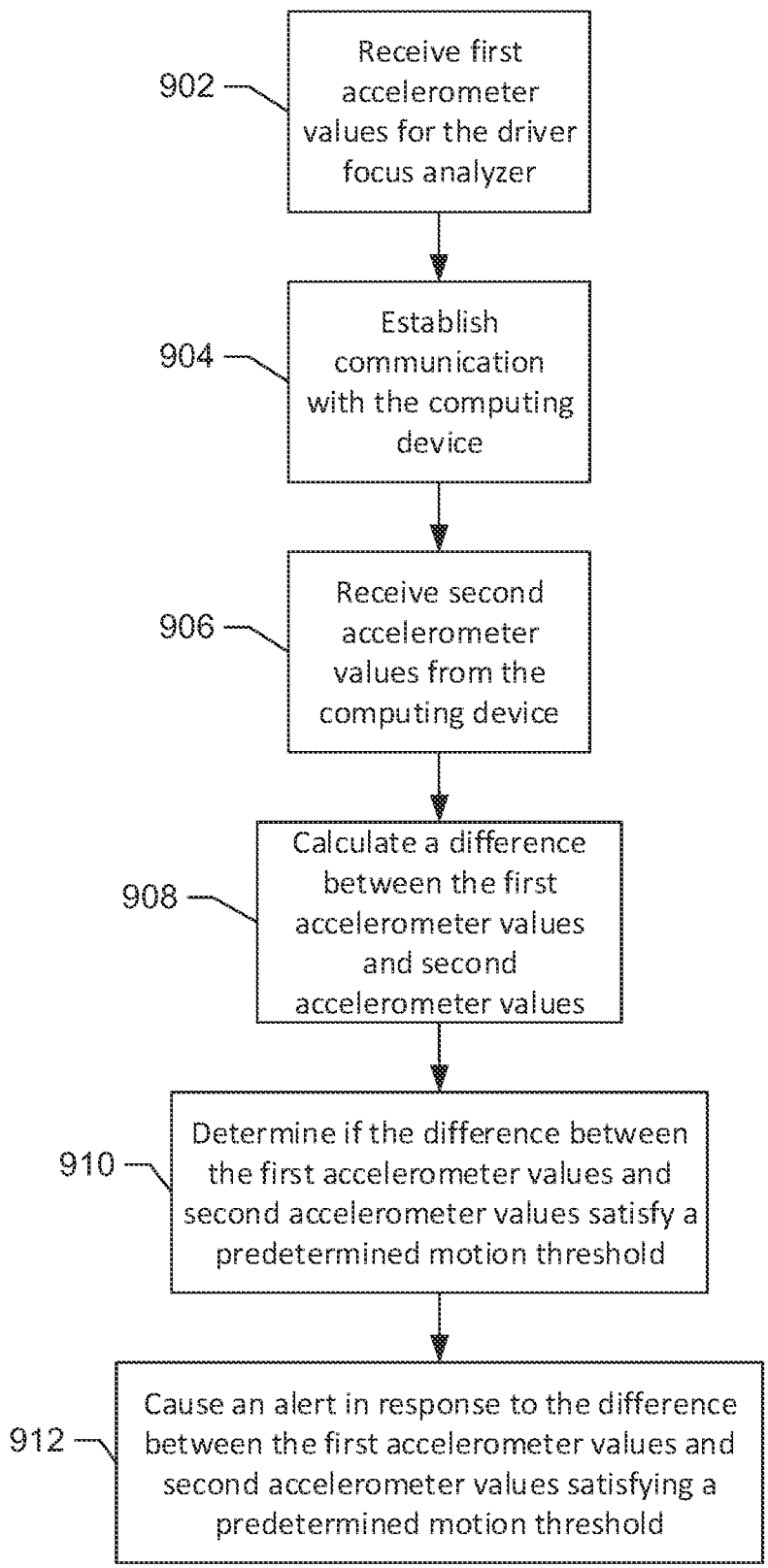
Figure 10:
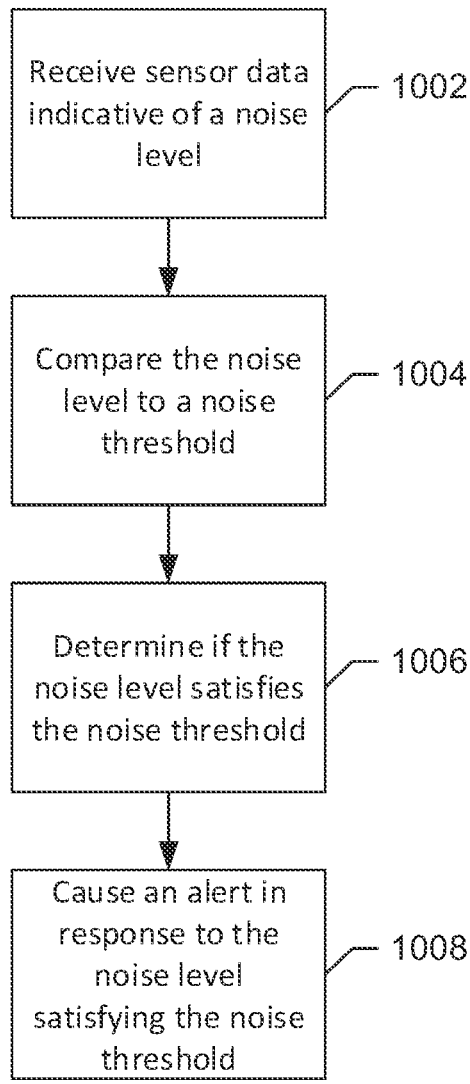
Figure 11:
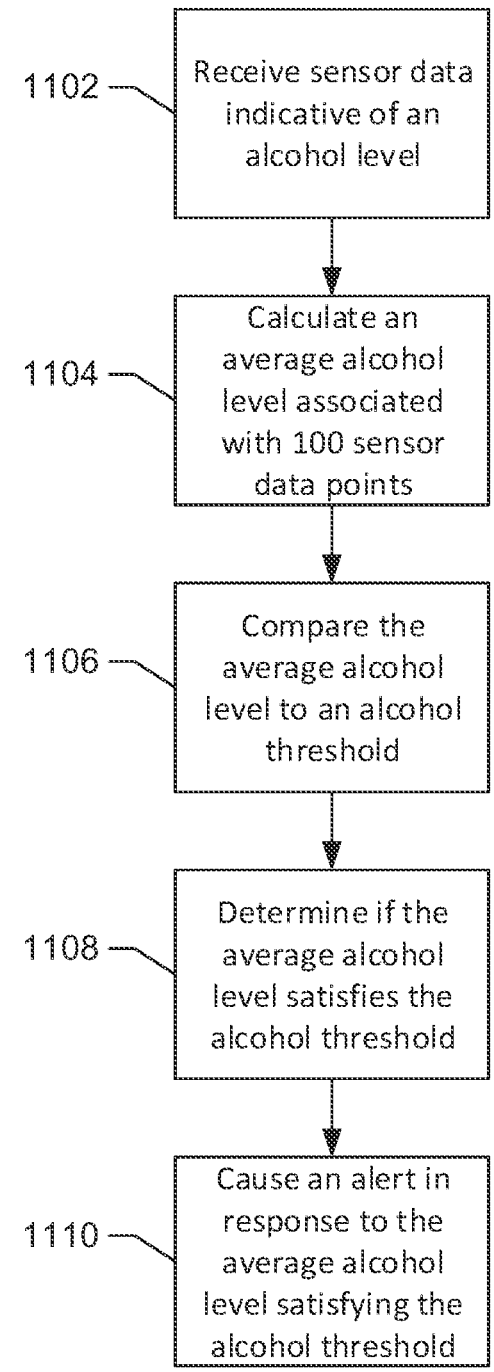

FIG. 7 illustrates a right side view of the head rest 300 according to an example embodiment. A sound sensor 308 may be disposed in the foam or padding of the head rest 300, such as in the left side of the head rest 300.

The driver focus analyzer may use one or more sensors to measure and determine conditions within the cabin of a vehicle which may be indicative of a distracted driver or could cause the driver to become distracted. Additionally or alternatively, the driver focus analyzer may sense intoxicants which may cause the driver to be unsafe for operation of the vehicle. The driver focus analyzer may cause an audio and/or visual alert to bring these unsafe conditions to the attention of the driver and/or passengers, so that corrective measures may be taken.

In some cases, a method of utilizing the driver focus analyzer according to an example embodiment may be provided. FIGS. 8-11 illustrate block diagrams of some activities that may be associated with examples of such methods. In some embodiments, the processing circuitry (which may include a processor capable of executing instructions stored in a non-transitory computer readable medium/memory) may be configured to implement a control algorithm for the driver focus analyzer according to the methods. In some example embodiments, the methods may include additional, optional operations, and/or the operations described above may be modified or augmented according to various embodiments described herein.

In an example embodiment, a method may include receiving sensor data at operation 802, comparing the sensor data to a predetermined threshold at operation 804, determining if the sensor data satisfies the predetermined threshold at operation 806, and causing an alert in an instance in which the sensor data satisfies the predetermined threshold at operation 808.

In some example embodiments, a method may include receiving first accelerometer values for the driver focus analyzer at operation 902, establishing communication with a computing device at operation 904, and receiving second accelerometer values from the computing device at operation 906. The method may also include calculating a difference between the first accelerometer values and the second accelerometer values at operation 908, determining if the difference between the first accelerometer values and the second accelerometer values satisfies a predetermined motion threshold at operation 910, and causing an alert in response to the difference between the first accelerometer values and the second accelerometer values satisfying the predetermined motion threshold at operation 912.

In an example embodiment, a method may include receiving sensor data indicative of a noise level at operation 1002, comparing the noise level to a noise threshold at operation 1004, determining if the noise level satisfies the noise threshold at operation 1006, and causing an alert in response to the noise level satisfying the noise threshold at operation 1008.

In some example embodiments, a method may include receiving sensor data indicative of an alcohol level at operation 1102, calculating an average alcohol level associated with 100 sensor data points at operation 1104, and comparing the average alcohol level to an alcohol threshold at operation 1106. The method may also include determining if the average alcohol level satisfies the intoxicant threshold at operation 1108 and causing an alert in response to the average alcohol level satisfying the alcohol threshold at operation 1110.

In an example embodiment, the CSS monitoring device may comprise a processor (e.g. the processor 204) or processing circuitry 202 configured to perform, for example, some or each of the operations (802-808, 902-912, 1002-1008, and 1102-1110) described above. The processor 204 may, for example, be configured to perform the operations (802-808, 902-912, 1002-1008, and 1102-1110) by performing hardware implemented logical functions, executing stored instructions, or executing algorithms for performing each of the operations. In some embodiments, the processor 204 or processing circuitry 202 may be further configured for additional operations or optional modifications to operations 802-808, 902-912, 1002-1008, and 1102-1110. In this regard, for example, the driver focus analyzer is at least partially contained in a portion of a vehicle seat.

In an example embodiment, the driver focus analyzer is at least partially contained in a head rest of a vehicle seat. In some example embodiments, the driver focus analyzer is at least partially contained in the headliner of a vehicle. In an example embodiment, the one or more sensors comprise at least one ultrasonic sensor, and the distance includes a measurement of a head of the driver from the sensor. In some example embodiments, the driver focus analyzer also includes a communication interface and a location sensor. The processing circuitry is further configured to receive location data associated with a computing device, receive location data from the location sensor, determine a range between the computing device and the driver focus analyzer, compare the range to a predetermined range threshold, determine if the range satisfies the predetermined range threshold and cause an alert in response to the range satisfying the predetermined range threshold. In some example embodiments, the driver focus analyzer also includes a communication interface and one or more motion sensors. The processing circuitry is further configured to receive motion data associated with a computing device, receive motion data from the one or more motion, determine a relative motion between the computing device and the driver focus analyzer, compare the relative motion to a predetermined motion threshold, determine if the relative motion satisfies the predetermined motion threshold, and cause an alert in response to the relative motion satisfying the predetermined motion threshold. In an example embodiment, the one or more sensors include at least two proximity sensors and the alert is caused in response to the distance measured by any of the at least two proximity sensors. In some example embodiments, the driver focus analyzer also includes one or more sensors configured to measure an intoxicant level proximate to the driver, and the processing circuitry is further configured to compare the intoxicant level to a predetermined intoxicant threshold, determine if the intoxicant level exceeds the predetermined intoxicant threshold, and cause the alert in response to determining that the intoxicant level exceeds the predetermined threshold. In an example embodiment, the driver focus analyzer also includes one or more sensors configured to measure an noise level proximate to the driver, and the processing circuitry is further configured to compare the noise level to a predetermined noise threshold determine if the noise level exceeds the predetermined noise threshold, and cause the alert in response to determining that the noise level exceeds the predetermined threshold. In some example embodiments, the one or more sensors include at least one alcohol sensor. In an example embodiment, the one or more sensors are configured to measure tetrahydrocannabinol (THC).

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. In cases where advantages, benefits or solutions to problems are described herein, it should be appreciated that such advantages, benefits and/or solutions may be applicable to some example embodiments, but not necessarily all example embodiments. Thus, any advantages, benefits or solutions described herein should not be thought of as being critical, required or essential to all embodiments or to that which is claimed herein. Although specific terms are employed herein, they are used in a generic and descriptive sense only and not for purposes of limitation.

That which is claimed:

1. A driver focus analyzer system comprising:
a headrest for a vehicle, wherein the headrest defines a left half side and a right half side;
a first proximity sensor positioned within the left half side of the headrest and configured to measure a left side driver distance corresponding to a position of a left side of a driver relative to the headrest;
a second proximity sensor positioned within the right half side of the headrest and configured to measure a right side driver distance corresponding to a position of a right side of the driver relative to the headrest;
an alert output device configured to generate an audio or visual output in response to an alert; and
processing circuitry configured to:
receive first sensor data from the first proximity sensor;
receive second sensor data from the second proximity sensor;
determine, based on the first sensor data, the left side driver distance between the left side of the driver and the headrest;
determine, based on the second sensor data, the right side driver distance between the right side of the driver and the headrest;
compare the left side driver distance to the right side driver distance to determine if a predetermined distance threshold is satisfied due to a head of the driver being turned from a field of view corresponding to safe operation of the vehicle, wherein the predetermined distance threshold is satisfied in an instance in which the left side driver distance is different than the right side driver distance; and
cause the alert in response to determining that the predetermined distance threshold is satisfied and a predetermined time threshold is satisfied, wherein the predetermined time threshold accounts for the driver adjusting position, the driver performing a blind spot check, or the driver looking briefly at signs or address information on a building.

2. A driver focus analyzer comprising:
a first proximity sensor positioned within a left half side of a headrest and configured to measure a left side driver distance corresponding to a posit ion of a left side of a driver relative to the headrest;
a second proximity sensor positioned within a right half side of the headrest and configured to measure a right side driver distance corresponding to a position of a right side of the driver relative to the headrest;
an alert output device configured to generate an audio or visual output in response to an alert; and
processing circuitry configured to:
receive first sensor data from the first proximity sensor;
receive second sensor data from the second proximity sensor;
determine, based on the first sensor data, the left side driver distance between the left side of the driver and the headrest;
determine, based on the second sensor data, the right side driver distance between the right side of the driver and the headrest;
determine, based on a comparison of the left side driver distance and the right side driver distance, a motion that corresponds to a head of the driver being turned from a field of view corresponding to safe operation of the vehicle;
determine if the motion satisfies a predetermined motion threshold, wherein the predetermined motion threshold is satisfied in an instance in which the left side driver distance is different than the right side driver distance; and cause the alert in response to the motion satisfying the predetermined motion threshold and a predetermined time threshold, wherein the predetermined time threshold accounts for the driver adjusting position, the driver performing a blind spot check, or the driver looking briefly at signs or address information on a building.

3. A method comprising:

providing a driver focus analyzer within a vehicle comprising:

a first proximity sensor positioned within a left half side of a headrest and configured to measure a left side driver distance corresponding to a position of a left side of a driver relative to the headrest;

a second proximity sensor positioned within a right half side of the headrest and configured to measure a right side driver distance corresponding to a position of a right side of the driver relative to the headrest;

an alert output device configured to generate an audio or visual output in response to an alert; and processing circuitry;

receiving first sensor data from the first proximity sensor;

receiving second sensor data from the second proximity sensor;

determining, based on the first sensor data, the left side driver distance between the left side of the driver and the headrest;

determining, based on the second sensor data, the right side driver distance between the right side of the driver and the headrest;

determining, based on a comparison of the left side driver distance and the right side driver distance, a motion that corresponds to a head of the driver being turned from a field of view corresponding to safe operation of the vehicle;

determining if the motion satisfies a predetermined motion threshold, wherein the predetermined motion threshold is satisfied in an instance in which the left side driver distance is different than the right side driver distance; and causing the alert in response to the motion satisfying the predetermined motion threshold and a predetermined time threshold, wherein the predetermined time threshold accounts for the driver adjusting position, the driver performing a blind spot check, or the driver looking briefly at signs or address information on a building.

\* \* \* \* \*